US00PP23740P3

(12) United States Plant Patent
Bradford

(10) Patent No.: US PP23,740 P3
(45) Date of Patent: Jul. 16, 2013

(54) INTERSPECIFIC TREE NAMED 'LATESWEET XX'

(50) Latin Name: ***Prunus* sp.**
Varietal Denomination: LATESWEET XX

(76) Inventor: Lowell Glen Bradford, Le Grand, CA (US)

( * ) Notice: Subject to any disclaimer, the term of this patent is extended or adjusted under 35 U.S.C. 154(b) by 76 days.

(21) Appl. No.: 13/374,022

(22) Filed: Dec. 8, 2011

(65) Prior Publication Data

US 2013/0152244 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,220 P2 10/2003 Bradford

*Primary Examiner* — Annette Para

(57) ABSTRACT

The present invention relates to an interspecific tree and more particularly to a new and distinct variety broadly characterized by a medium size, vigorous, hardy, and very productive tree. Being self-unfruitful, the present variety requires cross pollination from an apricot, interspecific, or plum that blooms during the late season. The present variety produces a very heavy bloom with an abundance of pollen to entice good bee activity to facilitate pollination. The fruit matures under the ecological conditions described during the last half of October, with first picking on Oct. 23, 2011. The fruit is uniformly medium in size, very dark red to purple in skin color, semi-clingstone in type, globose to oblate in shape, yellow in flesh color, firm in texture, and excellent in flavor.

1 Drawing Sheet

Botanical classification: *Prunus* sp.

Varietal denomination: 'LATESWEET XX'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'LATESWEET XX'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2004 one such house containing a 'September Yummy®' plum tree (U.S. Plant Pat. No. 14,220) was crossed by me in this manner. To pollinate this plum tree, I selected bouquets from several sources of apricot and interspecific hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2008 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'September Yummy' (U.S. Plant Pat. No. 14,220) plum, by being self-unfruitful and by producing fruit that is semi-freestone in type, juicy, firm in texture, and mostly yellow in flesh color, but is distinguished therefrom by producing fruit that is darker red in skin color, somewhat smaller in size, oblate instead of globose in shape, sweeter in flavor, and that matures about forty days later.

SUMMARY OF VARIETY

The present interspecific variety is characterized by a medium size, vigorous, hardy, and very productive tree. Being self-unfruitful, the present variety requires cross pollination from an apricot, interspecific, or plum that blooms during the late season. The present variety produces a very heavy bloom with an abundance of pollen to entice good bee activity to facilitate pollination. The fruit matures under the ecological conditions described during the last half of October, with first picking on Oct. 23, 2011. The fruit is uniformly medium in size, full purple in skin color, semi-clingstone in type, globose in shape, yellow in flesh color, firm in texture, and excellent in flavor.

DRAWING

The accompanying photograph consists of four whole fruits positioned to display the characteristics of the skin color and form, two half fruits divided to reveal the flesh and stone, typical leaves, and one inset depicting the blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the picking ripe on Oct. 23, 2011, on the original tree during its seventh growing season. The flower and bud descriptions were developed during the previous blooming season. All major color code designations are by reference to the Inter-Society Color Council, National Bureau of Standards. Common color names are also used occasionally.

PARENTAGE

Seed parent: 'September Yummy®' (U.S. Plant Pat. No. 14,220).

Pollen parent: Unknown.

TREE

Size: Medium, reaching and maintaining a height of 10' [3.05 m.] and a spread of 8' [2.44 m.] after seven growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable late seasonal blooming plum or interspecific, such as 'Black Majesty' plum (U.S. Plant Pat. No. 19,527).

Bearing: Regular bearer, no crop failures observed, weather dependent.

Trunk:

*Size.*—Medium, reaching a maximum diameter of 4½" [114.3 mm.] after the seventh growing season.

*Texture.*—Shaggy.

*Bark color.*—A Dark grayish brown [62. d.gy.Br] and Grayish brown [61. gy.Br] variegation with Light yellowish brown [76. l.yBr] crevices present.

*Lenticels.*—Approximate Number Per Square Inch: 8. Color: Light yellowish brown [76. l.yBr]. Size: ⅛" [3.2 mm.] to 5/16" [7.9 mm.]. Shape: Eye-shaped, elongated.

Branches:

*Size.*—Diameter of central leader 3" [76.2 mm.] measured 12" above the first hanger, which itself has a maximum diameter of ¾" [19.1 mm.].

*Texture.*—Smooth on first and second year wood, increasing roughness with age.

*Color.*—1st Year Wood Topside: Grayish red [19. gy.12]. 1st Year Wood Underside: Brilliant yellow green [116. brill.YG]. Older Wood: A Dark grayish brown [62. d.gy.Br] and Grayish brown [61. gy.Br] variegation with Light yellowish brown [76. l.yBr] crevices present.

*Lenticels.*—Number Per Square Inch: About 80 on second year wood. Color: Light yellowish brown [76. l.yBr]. Size: 1/64" [0.4 mm.] to 1/32" [0.8 mm.]. Shape: Eye-shaped, elongated.

Leaves:

*Size.*—Medium to large. Average Length: 4" [101.6 mm.]. Average Width: 2⅛" [54 mm.].

*Arrangement.*—Alternate.

*Thickness.*—Medium.

*Form.*—Elliptical.

*Apex.*—Acuminate.

*Base.*—Acute to rounded.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Moderate yellow green [120. m.YG].

*Stipules.*—Number: Uusually 2 per leaf, up to 6 per growing tip. Average Length: ¼" [6.4 mm.]. Color: Light yellow green [119. l.YG] becoming Moderate yellow green [120. m.YG] with age.

*Glands.*—Number: 1 to 4 per leaf, mostly 2. Position: Both alternately and oppositely positioned on petiole and the base of leaf blade. Size: Medium. Form: Globose. Color: Moderate olive green [125. m.OlG] becoming Brownish gray [64. brGy] in the center with age. Leaf buds. — Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—1" [25.4 mm.].

*Number of petals.*—Five, no double blossoms observed.

*Petal shape.*—Oval to circular.

*Petal margin.*—Entire, slightly wavy.

*Average petal diameter.*—½" [12.7 mm.].

*Average petal length.*—9/16" [14.3 mm.].

*Petal apex.*—Rounded.

*Petal base.*—Obtuse.

*Petal color.*—White [263. White] on both sides.

*Anther color.*—Light orange yellow [70. l.OY].

*Stigma color.*—Brilliant greenish yellow [98. brill.gY].

*Sepal color.*—Brilliant yellow green [116. brill.YG] on the outer surface with Brownish pink [33. brPk] toward the edges on some.

*Sepal length.*—3/16" [4.8 mm.].

*Sepal width.*—5/32" [4.0 mm.].

*Sepal apex.*—Rounded to elliptical to match the width and length.

*Sepal margin.*—Fairly smooth with slight serrations toward the apex.

*Average pistil length.*—⅝" [15.9 mm.].

*Average stamen length.*—7/16" [11.1 mm.].

*Fragrance.*—Moderate.
*Bloom density.*—Very heavy.
*Number per cluster.*—2 to 10, average 5.
*Pollen production.*—Abundant, good enticement to bees.
*Blooming period.*—Late, three days after 'Santa Rosa' plum (unpatented).
*Onset of bloom.*—One percent on Mar. 7, 2011.
*Date of full bloom.*—Mar. 16, 2011.
*Duration of bloom.*—One to two weeks, dependent on ambient temperature.

FRUIT

Maturity when described: Picking ripe, Oct. 23, 2011.
Date of first picking: Oct. 23, 2011.
Date of last picking: Nov. 6, 2011.
Size: Uniform, medium.
*Average diameter axially.*—2¼" [57.2 mm.].
*Average diameter across cheek plane.*—2⁷⁄₁₆" [61.9 mm.].
*Average diameter across suture plane.*—2⁷⁄₁₆" [61.9 mm.].
*Typical weight.*—4.6 ounces [130.4 grams].
Form: Uniform, oblate, mostly symmetrical.
*Longitudinal section form.*—Oblate.
*Transverse section through axial diameter.*—Round.
Suture: An inconspicuous line located in a shallow groove extending from the base to the apex, slightly sharper toward both the base and apex.
Ventral surface: Rounded, lipped toward the base and apex on both sides.
Lips: Slightly unequal.
Cavity: Flaring to somewhat elongated in the suture plane, suture showing on one side.
*Depth.*—³⁄₁₆" [4.8 mm.].
*Breadth.*—⁹⁄₁₆" [14.3 mm.].
Base: Truncate, slightly cordate if viewed parallel to the suture.
Apex: Rounded to somewhat truncate.
Pistil point: An inconspicuous Pale yellow green [121. p.YG] dot located at the end of the suture.
Stem: Medium.
*Average length.*—½" [12.7 mm.].
*Average width.*—⅛" [3.2 mm.].
Skin:
*Thickness.*—Medium.
*Surface.*—Smooth.
*Tenacity.*—Tenacious to the flesh.
*Astringency.*—Slight.
*Tendency to crack.*—None observed.
*Color.*—Very dark red [17. v.d.R] over a Dark red [16. d.R] background with a moderate amount of Pale yellow green [121. p.YG] freckling throughout.
*Bloom.*—Abundant.
Flesh:
*Color.*—Brilliant orange yellow [67. brill. OY].
*Surface of pit cavity.*—Covered with Pale greenish yellow [104. p.gY] fibers.
*Amygdalin.*—Scarce.
*Juice.*—Moderate, rich.
*Texture.*—Firm, crisp, meaty.
*Fibers.*—Few, fine, tender.
*Ripens.*—Slightly earlier toward the apex.
*Flavor.*—Sweet with moderate acid, typically 22 brix.
*Aroma.*—Very slight.
*Eating quality.*—Excellent.

STONE

Type: Semi-freestone.
Form: Oval.
Hilum: Narrow.
Base: Acute.
Apex: Rounded with a sharp ¹⁄₁₆" [1.6 mm.] tip.
Sides: Equal.
Surface: Rough throughout, a vertical ridge on each side of the dorsal fin, another vertical ridge on each side closer to the ventral edge, a flat fin protruding on the ventral edge toward the apex.
External color of stone: Moderate yellowish brown [77. m.yBr] when dry.
Pit wall color when cracked: Dark yellow [88. d.Y].
Cavity surface color: Light yellowish brown [76. l.yBr].
Average pit wall thickness: ⅛" [3.2 mm.].
Average width: ⅝" [15.9 mm.].
Average length: ⅞" [22.2 mm.].
Average breadth: ⅜" [9.5 mm.].
Tendency to split: None observed.
Kernel:
*Form.*—Oval.
*Skin color.*—Strong yellowish brown [74. s.yBr].
*Pellicle color.*—Dark yellowish brown [78. d.yBr].
*Vein color.*—Dark yellowish brown [78. d.yBr].
*Taste.*—Slightly bitter.
*Viable.*—Yes.
*Average width.*—⁷⁄₁₆" [11.1 mm.].
*Average length.*—⁹⁄₁₆" [14.3 mm.].
*Amygdalin.*—Scant.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its seed parent, 'September Yummy' (U.S. Plant Pat. No. 14,220) plum, by being self-unfruitful and by producing fruit that is semi-freestone in type, juicy, firm in texture, and mostly yellow in flesh color, but is distinguished therefrom by producing fruit that is darker red in skin color, somewhat smaller in size, oblate instead of globose in shape, sweeter in flavor, and that matures about forty days later.

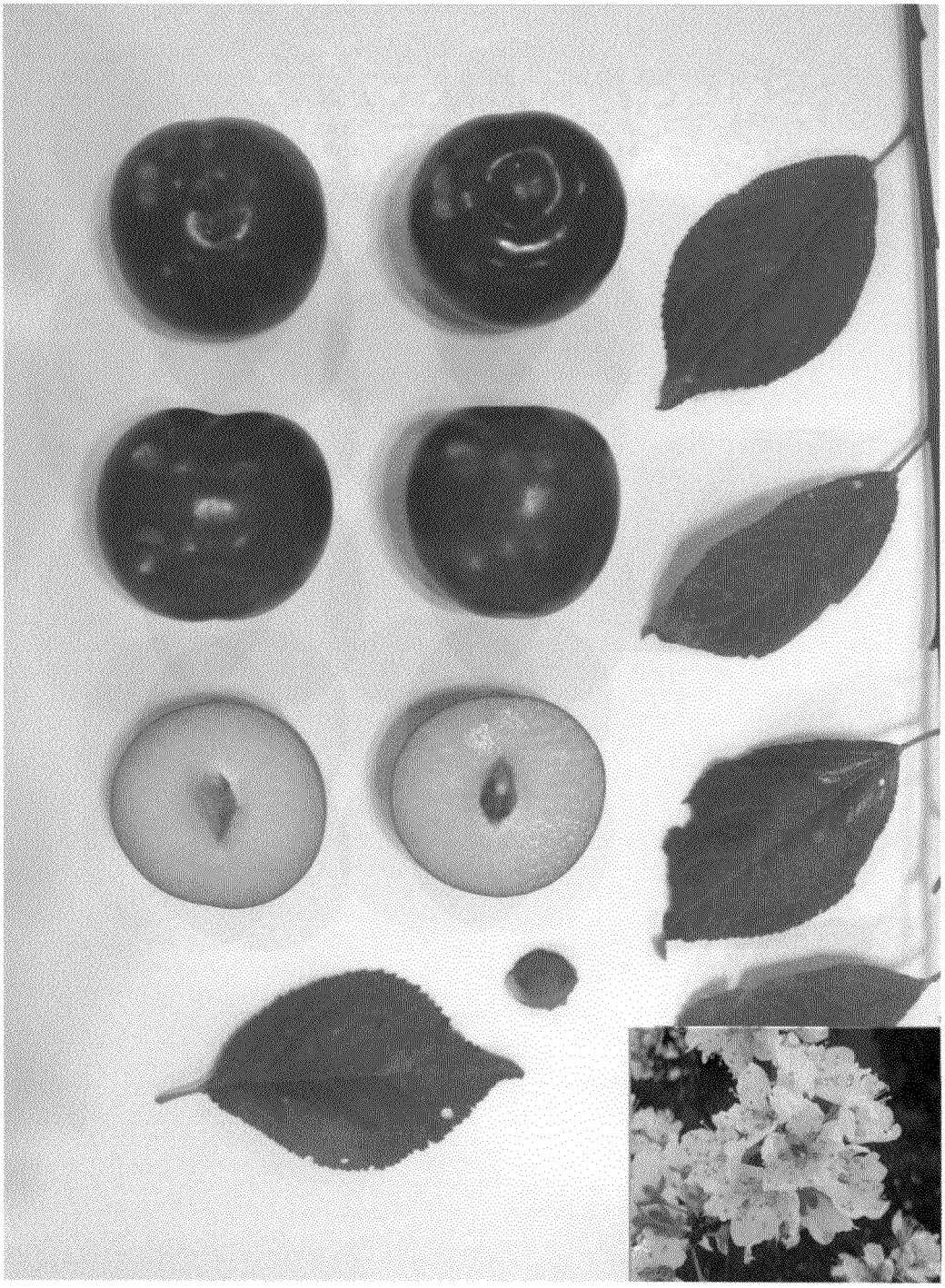

* * * * *